United States Patent [19]

Bischoff et al.

[11] Patent Number: 4,666,940

[45] Date of Patent: May 19, 1987

[54] ACARICIDAL CLEANING COMPOSITION FOR CONTROLLING HOUSE DUST MITES AND PROCESS OF USING

[75] Inventors: Edelbert Bischoff, Kirchheim-Bolanden; Gert Wetter, Worrstadt-Rommersheim, both of Fed. Rep. of Germany

[73] Assignee: Werner & Mertz GmbH, Mainz, Fed. Rep. of Germany

[21] Appl. No.: 767,476

[22] Filed: Aug. 20, 1985

[30] Foreign Application Priority Data

Aug. 20, 1984 [DE] Fed. Rep. of Germany ....... 3430611

[51] Int. Cl.⁴ .................. A01N 31/08; C11D 3/48; E04B 1/72
[52] U.S. Cl. .................... 514/544; 252/88; 252/89.1; 252/106; 252/107; 252/173; 252/174; 252/174.25; 252/DIG. 14; 514/532; 514/533
[58] Field of Search ......... 252/88, 106, 107, 170, 174, 252/174.25, 89.1, 173; 514/532, 533, 544

[56] References Cited

U.S. PATENT DOCUMENTS

| | | | |
|---|---|---|---|
| 3,418,243 | 12/1968 | Hoxie | 252/154 |
| 3,630,919 | 12/1971 | Sheaffer et al. | 252/109 |
| 3,723,358 | 3/1973 | Morgan | 252/546 |
| 3,736,259 | 5/1973 | Buck | 252/140 |
| 3,775,052 | 11/1973 | Van Paassen | 8/137 |
| 3,843,563 | 10/1974 | Davies | 252/547 |
| 3,868,336 | 2/1975 | Mazzola | 252/527 |
| 4,002,571 | 1/1977 | Anderle | 252/90 |
| 4,028,261 | 6/1977 | Peterson | 252/106 |
| 4,161,449 | 7/1979 | Smith | 252/8.6 |
| 4,252,694 | 2/1981 | Lewis | 252/545 |
| 4,289,641 | 9/1981 | Hooper | 252/96 |
| 4,304,675 | 12/1981 | Corey | 252/8.6 |
| 4,347,153 | 8/1982 | Hooper | 252/174.25 |
| 4,493,781 | 1/1985 | Chapman | 252/88 |
| 4,552,777 | 11/1985 | Dente | 427/393.1 |

FOREIGN PATENT DOCUMENTS

| | | |
|---|---|---|
| 1145252 | 4/1983 | Canada . |
| 1163192 | 3/1984 | Canada . |
| 1368657 | 10/1974 | United Kingdom . |
| 2042893 | 10/1980 | United Kingdom . |
| 2126898 | 4/1984 | United Kingdom . |

OTHER PUBLICATIONS

Heller-Haupt, A. et al., "Tests of Acaricides Against House Dust Mites", *J. Med. Entomol.*, vol. 11, No. 5, pp. 551-558, Nov. 1974.

Leysen, M. Th. et al., "Susceptibility of the House-Dust Mite to Pesticides and Disinfectants", *Acta Allergol.*, vol. 29, No. 6, pp. 455-461, 1974.

*Primary Examiner*—Dennis L. Albrecht
*Attorney, Agent, or Firm*—Ladas & Parry

[57] ABSTRACT

The invention relates to a cleansing composition for treating textile surfaces of interior furnishings, said composition including a liquid, foam-type or pulverulent cleanser and including benzyl benzoate as an acaricidal component as well as a solid which causes a pulverulent residue of a particle size suitable for oral ingestion by house dust mites. Water is a predominant component of a liquid carrier for the liquid or foam-type cleanser or of a liquid content of the pulverulent cleanser. A method for killing house dust mites comprises applying said composition to textile surfaces of interior furnishing, e.g., carpets and mattresses.

17 Claims, No Drawings

ACARICIDAL CLEANING COMPOSITION FOR CONTROLLING HOUSE DUST MITES AND PROCESS OF USING

BACKGROUND OF THE INVENTION

Health problems due to allergies have been increasing recently. The allergy to house dust plays a particularly large role here. This is caused by the excrements of the house dust mite, which contains allergens and form extremely fine dust aerosols. The occurrence of the house dust mites is more and more frequently observed in the industrial countries. Possible causes of this are the microclimate in dwelling rooms and the decrease in natural enemies of the house dust mites as the result of hygienic measures such as, for example, vacuum-cleaning. House dust mites live wherever they can hide and where they find suitable nourishment and a microclimate suitable for them with respect to atmospheric humidity and warmth. The result is that textile materials represent their preferred places of stay, that is to say, beds, upholstered furniture, carpets and the like.

There are so far no satisfactory agents for controlling house dust mites. Due to their composition, the known agents are suitable only for the treatment of small areas such as, for example, the mattresses of beds. They are applied by spraying the surface. However, a closer investigation shows that the treatment of beds—even if it should be effective there—can solve only a part of the problem. Upholstered furniture which, as a rule, is less frequently and less intensively cleaned than beds, is in many cases heavily infested. Moreover, very fine dust is continuously whirled up from carpets as the result of walking on them; this means that allergic persons are troubled day and night.

The tendency of the house dust mite to hide and to creep under such objects has the result that a treatment of the surfaces of the said interior furnishings is not sufficient. A carpet must be treated right in the depth, and mattresses and upholstered furniture must be treated in a layer of 1 to 2 cm thickness, where the majority of the mites are present.

On the other hand, a preparation (agent) which is intended to be capable of destroying house dust mites must be physiologically compatible with and toxicologically acceptable to humans who are nearby.

PRIOR ART

Two commercially available preparations which contain active substances based on organic solvents and are applied by spraying the mattresses are known for controlling house dust mites in beds. The actual active substances consist in one case of phenol derivatives and a number of natural essential oils and, in the other case, of the antibiotic natamycin (cf. A. Pénaud et al.; Methods of destroying house dust pyroglyphid mites, Clinical Allergy (1975), pages 109 to 114; A. Pénaud et al; Results of a controlled trial of the acaricide Paragerm on Dermatophagoides sp. in dwelling houses, Clinical Allergy (1977), pages 49 to 53; Danièle de Saint-Georges-Gridelet; Mise au point d'une stratégie de controôle de l'acarien des poussieres (Dermatophagoides pteronyssinus) par utilisation d'un fongicide [Review of a strategy for controlling the dust acarid by use of a fungicide], Acta Oecologica/Oecol. Applic. (1981), pages 117 to 126).

The range of application of both agents is restricted, inasmuch as organic solvents cannot be applied, for safety reasons, to large areas and because phenol derivatives and essential oils are not satisfactory for physiological and sometimes odor reasons. Moreover, an antibiotic, such as natamycin, is in principle not applied to attack the house dust mites themselves but rather the fungi which populate the skin scales used by the mites as nourishment and thus provide prepare this nourishment for the mites. As tests show, this does not lead to satisfactory destruction of the mites.

In addition, gamma-hexachlorocyclohexane, pirimiphos methyl, diethyl-m-toluamide, dibutyl phthalate and benzyl benzoate have been described in the literature as active substances which destroy mites (cf. Agnes-Heller-Haupt et al., Tests of acaricides against house dust mites, J. Med. Entomology, Volume 11, No. 5, 551 to 558 (1974). From among these substances, the two first-mentioned are indeed effective, but they cannot be used in the household for reasons of toxicology and envirohmental hygiene. It was also impossible to convert the remaining three active substances into products for practical use.

European Pat. No. 17,315 has disclosed that normal insecticides, such as pyrethrins or DDT, are relatively ineffective against house dust mites. According to this patent specification, benzyl benzoate is regarded as a suitable active substance, and the aim of that patent is to diminish a disadvantage of this compound, namely the relatively high vapor pressure, in order to achieve longer retention of the substance. For this purpose, combinations of benzyl benzoate with fatty acid esters and a fungicidal agent in a non-aqueous preparation are proposed therein.

According to British Pat. No. 1,368,657, a similar object is said to be achievable by adding non-volatile polyalkylene glycols or non-volatile ethers or esters thereof to the benzyl benzoate. However, this has caused considerable disadvantages in the use of the beds, and these are documented in detail in the said European Pat. No. 17,315. In both literature references, the carrier substances used are volatile organic solvents.

The main area of application of the agent according to European Pat. No. 17,315 is the prophylactic treatment of industrial materials used for the manufacture of mattresses and the like. Thus, the intention is prevention of the infestation my mites. For this reason, lowering the vapor pressure of benzyl benzoate is again of great importance in this case. Likewise, the use of those organic solvents is possible there, ie. in the factory area, which are physiologically unacceptable, such as, for example, chloroform or carbon tetrachloride. It is also indicated in this patent that it might be useful for the case of textile finishing to apply mixtures of benzyl benzoate and vapor pressure-reducing additives in a solid form, for example dispersed with a suitable powder, such as talc or aerosol. However, this suggestion is not discussed further and does not provide any technical teaching regarding the subject of the application.

Summarizing, the starting situation for the subject of the application in the light of the state of the art was as follows:

Normal known insecticides are not effective against house dust mites and/or are toxicologically objectionable or have such a pervading odor that they cannot be used in the domestic area. Among the other substances regarded as acaricidally effective, certain esters such as, for example, benzyl benzoate, dibutyl phthalate and the like, would in fact be acceptable under physiological aspects. Attempts have therefore also already been made, for example, for benzyl benzoate, to overcome some of the disadvantages inherent in this compound—relative to the envisaged type of application—by special recipe formulations. These disadvantages include a relatively high vapor pressure which is an adverse factor above all if it is desired to let the compound act prophylactically for textile finishing, ie. over a prolonged period (cf. European Pat. No. 17,315). However, it was not possible to implement this type of textile finishing in practice. Moreover, it also did not solve the problem that house dust mites are already present in most households and that these have already infested the carpets, upholstered furniture and beds. The hitherto known commercial products are—as stated above—intended only for the treatment of beds and, because of their organic solvent content, can also be applied only to relatively small restricted surface areas.

One of the problems to be solved according to the invention was therefore the discovery of acaricidal agents which can be applied by laymen everywhere in the household, if possible without significant additional work effort, that is to say within the scope of a normal cleaning procedure.

The life cycle of the house dust mites extends over a period of about 3 months. Including the hatching of eggs which have not been killed, an activity action period of the acaricide of two to three weeks is necessary in order to destroy a mite population or to diminish it to such an extent that the inhabitants of the mite-infested rooms and objects are no longer troubled. A further problem to be solved according to the invention was therefore the discovery of an agent which kills house dust mites and the components of which are acceptable with respect to physiological compatibility with humans, even on repeated application.

In selecting the acaricidal active substances, the physiologically well investigated benzyl benzoate might have been quite a good idea. Experiments with this compound for use in hitherto conventional cleansers, however, raised considerable problems: the high-boiling fluid "stuck" to all substrates coming into contact with it, for example carpet fibers, mattress fabrics and upholstery coverings, and resulted in an extremely enhanced tendency to pick up dirt. The additional use of this substance caused the cleaning procedure to have the opposite effect, since a more than proportionally intensified dirt redeposition started immediately after the application of the particular agents. In this respect, dibutyl phthalate showed similar disadvantages. A third problem to be solved according to the invention was therefore the provision of an agent without a tendency to stick.

A further problem in the additional use of benzyl benzoate and dibutyl phthalate resulted from the fact that conventional liquid cleansers, the cleaning effect of which is essentially to be ascribed to the surfactants present in them, lose their original cleaning effect. (This may be connected with the fact that a major part of the surfactants is consumed in emulsifying benzyl benzoate or dibutyl phthalate and is no longer available for dirt emulsification.) In order to eliminate this disadvantage, the applicant attempted to increase the proportion of surfactants. However, this led to new disadvantages since the dirt redeposition behavior became even more unfavorable.

The applicant then found that this first series of problems can be solved when a cleanser with acaricidal active substances, for example benzyl benzoate, is formulated in such a way that pulverulent dry residues, which do not have a tendency towards enhanced dirt redeposition, result from the cleanser/active substance combination after application.

In addition to the formulation technology aspect of the subject of the application, as discussed, however, further requirements, in particular with respect to the acaricidal action, for example of the benzyl benzoate and the dibutyl phthalate, had to be met. In this connection, the following can be stated: since destruction of the mites by the action of only the vapor of benzyl benzoate is not possible (compare the literature quoted above), other means of applying the active substance had to be found. Mites can admittedly be killed by immersion in a solution containing n active substance; however, toxic liquid carrier materials such as, for example, organic solvents cannot be used here. On the other hand a treatment by immersion in aqueous fluids is successful only if the fluid in fact reaches the mites; to achieve this, the fluid should be present at every point of the article to be treated, and it should also completely wet the mites and their surroundings. The achievement of this object was therefore a further problem in the provision of a novel agent for the destruction of house dust mites.

As the applicant has found, the mites can be destroyed by oral ingestion of the acaricidal active substance. Since they move within their living space, they also come to existing solid active substance fractions which they did not reach directly during the treatment itself. In this connection, a further problem to be solved was the provision of an agent for destroying house dust mites, the resulting pulverulent residue of which after application is accepted by the mites as fodder, without having any repellent action on them.

SUMMARY OF THE INVENTION

All the problems discussed above, both with respect to the formulation technology and with respect to getting the acaricidal active substance to the mites, are now solved by the subject of the present application, namely by an agent for destroying house dust mites which comprises a combination of an acaricidal active substance and a liquid, foam-type or pulverulent cleanser for textile of interior furnishing surfaces, its pulverulent residue (after drying or application) having a mean particle size which is suitable for oral ingestion by the house dust mites.

A cleansing composition as defined above according to the invention ensures inter alia that enhanced dirt redeposition (due to "sticking" of the acaricidal active substances) is avoided and that the pulverulent residue resulting after drying or application is not only suitable for oral ingestion by the mites, due to its particle size, but it is also accepted by them as fodder.

For example, it was possible to prove experimentally that mites are immobilized and killed within one hour after the ingestion of particles of an inert carrier material which contains 1% of its weight of benzyl benzoate.

The agent according to the invention, its further developments and its application are discussed in detail below.

The preferred carrier fluid in the house dust mite-destroying agent according to the invention (in the case of a liquid or foam-type cleanser) is water or (in the case of a pulverulent cleanser) is predominantly aqueous, ie. contains at least 50% by weight of water.

As the acaricidal active substance (component A below), high-boiling esters can be used, in particular benzyl benzoate, benzyl salicylate, phenyl benzoate, phenyl salicylate as well as mixed and simple phthalates such as, for example, dimethyl phthalate, diethyl phthalate, dibutyl phthalate, dioctyl phthalate, diisodecyl phthalate, diallyl phthalate or benzyl butyl phthalate. The quantity of the acaricidal active substance present in the agent according to the invention can vary. In general it amounts to 1 to 20 percent by weight, relative to the composition according to the invention. A quantity range from 1 to 6 percent by weight is preferred. A quantity range from 2 to 6 percent by weight has proved particularly suitable.

The liquid, foam-type pulverulent cleanser, present according to the invention, for textile surfaces of interior furnishings, with water as the predominant carrier fluid, is in each case a particularly matched recipe formulation for meeting the abovementioned requirements and at the same time providing the desired pulverulent residue having the suitable mean particle size after drying or application.

This mean particle size of the pulverulent residue after drying or application is in general 2 to 100 μm. A size range from 10 to 50 μm is here particularly preferred.

In order to obtain the desired pulverulent residue, the particular recipe formulation according to the invention is essentially based on the following components:

A. Acaricidal active substance: 1 to 20 percent by weight, in particular 1 to 6 percent by weight.

B. Water:
  for a liquid cleanser, 10 to 90% by weight, in particular 40 to 70% by weight;
  for a foam-type cleanser, 10 to 90% by weight, preferably 60 to 90% by weight, in particular 70 to 90% by weight;
  for a pulverulent cleanser, 5 to 60% by weight, in particular 10 to 30% by weight;

C. Dissolved or dispersed plastic:
  for a liquid cleaners, 5 to 90% by weight, in particular 20 to 60% by weight;
  for a foam-type cleanser, 1 to 80% by weight, in particular 5 to 10% by weight.
  Inorganic or organic solid:
  for a liquid cleanser, only in some cases, 0.5 to 20% by weight;
  for a foam-type cleanser, 0.5 to 20% by weight, in particular 1 to 5% by weight;
  for a pulverulent cleanser, 20 to 80% by weight, in particular 30 to 70% by weight.

D. Surfactants:
  for liquid and foam-type cleaners, 0.05 to 10% by weight, in particular 2 to 5% by weight;
  for a pulverulent cleanser, 0.05 to 10% by weight, in particular 0.05 to 1% by weight.

E. Anti-foam:
  for a liquid cleanser, 0.2 to 5% by weight, in particular 0.3 to 1% by weight, and if appropriate F. optional additives, such as a perfume (in particular 0.2% by weight), preservative (in particular 0.2% by weight) and thickener (in particular 0.1 to 2% by weight).

As a constituent for dissolving fatty dirt, a pulverulent cleanser preferably also contains, for example, white spirit in a quantity of 1 to 30% by weight, in particular 5 to 20% by weight. The preferred propellant in a foam-type cleanser is, for example, propane or butane in a quantity of 5 to 20% by weight, in particular 7 to 13% by weight.

The following may be mentioned as examples of the above component C: dissolved organic or inorganic polymers, such as xanthan gum or water-glass; acrylates from aqueous acrylate dispersions; inert materials, such as silicates, for example montmorillonite, amorphous silica, SiO2 in the form of quartz sand or siliceous earth, or carbonates, for example, precipitated or ground mineral chalk; high surface-area substances, such as cellulose powder, ground plastic foams (for example of urea/formaldehyde resin), plastic powders (for example of polyamide, polyurethane or polyethylene), flours of wood or corn cobs, and non-swellable starch. The following should also be mentioned: sodium aluminum silicates (types of molecular sieve), polishing alumina, aluminum oxide, borax; and organic macromolecular products, for example polystyrene, polypropylene and polyvinyl resins. According to the invention, it is possible that one or more of these components C are present in the recipe formulation.

In detail, these additions C have the purpose to ensure that, after drying or application of the agents according to the invention, a pulverulent residue results in which the acaricidal active substance is present in a solid form (occluded, absorbed or adsorbed) and specifically in the mean particle size, according to the claim, which can be ingested by the house dust mite.

By their capacity to form a pulverulent residue (together with the acaricidal active substance), the component C present according to the invention markedly differs from the film formers of hitherto conventional cleansers for textile substrates; with such conventional cleansers, for example liquid cleansers, it is in fact desired that the dry residue forms a film, that is to say the textile fiber is provided with a dirt-repelling coating. By contrast, such film formation is not desired in the case of the subject of the application, because the acaricidal active substance then adhering to the textile fiber would no longer be available for oral ingestion by the mites. In addition, the agent according to the invention differs from the category of those conventional textile cleansers in which the dry residue forms solids which can be sucked off as easily as possible (in the case of these conventional cleansers, larger flock-like particles, more widely exposed to the air stream are in fact desired); by contrast, the mean particle size of the pulverulent residue should not exceed a certain limit in the case of the subject of the application, because otherwise the mites are unable to ingest it. On the other hand, an unduly large proportion of very fine particles should also be avoided, because otherwise there is a tendency towards strong adhesion of the particles to the textile fibers and hence to a brightening of, for example, dark-colored fabrics.

The surfactants (component D) used for the special recipe formulation can be the anionic, non-ionic, cationic or amphoteric substances conventional in the field of textile cleansers. Examples of anionic surfactants to be mentioned are: sulfonated aromatic hydrocarbons, for example n-alkylbenzenesulfonate; sulfonated aliphatic hydrocarbons, for example secondary alkanesulfonate; sulfonated alpha-olefin, for example an olefinsulfonate; sulfated fatty alcohol, for example sodium lauryl-sulfate; sulfated fatty alcohol ether, for example sodium lauryl polyglycol ether-sulfate; sulfonated fatty acid methyl esters, for example the methyl ester of sulfonated palm kernel fatty acid; sulfonated maleic acid esters, for example lauryl sulfosucinnate; carboxymethylated fatty alcohol polyglycol ethers, for example lauryl polyglycol ether-acetate. Examples of non-ionic surfactants to be mentioned are: fatty alcohol ethoxylate, alkylphenol ethoxylate, fatty acid ethoxylate, fatty acid alkylolamide, fatty acid alkylolamide ethoxylate, fatty amine ethoxylate, and polyalkylene oxide block polymers. Quaternary ammonium compounds may be mentioned as cationic surfactants. Betaines are examples of ampholytes.

The antifoam (component E) present in the recipe formulation can also be of the conventional type. Fatty acids, for example commercially available mixtures of $C_{12}$-$C_{18}$-fatty acids in the form of their sodium salts (soaps), are particularly preferred here. Regarding the antifoam effect of soaps, see Helmut Statche, Tensid-Taschenbuch [Surfactant handbook], Munich-Vienna (1979), page 201.

Depending on whether the cleanser present according to the invention is in the form of a fluid or foam or powder, the following explanations should also be given for the individual case:

1. Liquid cleanser (acaricidal carpet cleaner)

The acaricidal active substance is incorporated in the aqueous medium. As a result, the mites are killed when they are immersed in the fluid, that is to say on dermal contact. At the same time, the pulverulent residue which results after drying of the fluid and has the appropriate mean particle size has the effect that it is also orally ingested by the mites and is active also in this way. Those mites are then also affected which were not wetted by the fluid itself or which migrate in from untreated areas after the fluid has dried.

2. Foam-type cleanser (acaricidal upholstery and mattress cleanser)

Similar aspects as described above under 1 are applicable here, but it is not intended in this case to effect extensive wetting of the objects to be treated; immersion is thus possible only in the superficial region.

The agent acts here mainly after drying, via the pulverulent residue having the particle size which can be orally ingested by the mites. The pulverulent residue trickles through the cavities of the textile fabric in which mites also are present, and is there ingested by them.

3. Pulverulent cleanser (acaricidal carpet cleaner)

In this embodiment, extensive moistening should altogether be avoided. As a result, re-use as soon as possible and milder treatment of sensitive fabrics is ensured. The acaricidal action in this case is based only on oral ingestion by the mites. For this reason, the mean particle size of the pulverulent residue after drying or application (on the adsorptively bonded quantity of fluid) is here particularly important, so that the major part of the powder can be orally ingested by the mites.

Agents according to the invention (for destroying house dust mites) of the following composition have proven particularly suitable:

|  | % by weight | % by weight |
|---|---|---|
| (I) Acaricidal carpet cleaner (pulverulent) | | |
| Cellulose powder | 20 to 80 preferably | 30 to 70 |
| Water | 5 to 60 preferably | 10 to 30 |
| White spirit | 1 to 30 preferably | 5 to 20 |
| Acaricidal active substance | 1 to 20 preferably | 2 to 6 |
| Surfactant | 0.05 to 5 preferably | 0.05 to 1 |
| Perfume | 0.2 | |
| Preservative | 0.2 | |
| (II) Acaricidal carpet cleaner (liquid) | | |
| Water | 10 to 90 preferably | 40 to 70 |
| Soap (antifoam) | 0.5 to 5 preferably | 0.5 to 1 |
| Surfactant | 1 to 10 preferably | 2 to 5 |
| Acaricidal active substance | 1 to 20 preferably | 2 to 6 |
| Polymer, 40% | 5 to 90 preferably | 20 to 60 |
| Perfume | 0.2 | |
| Preservative | 0.2 | |
| (III) Acaricidal upholstery and mattress cleanser (foam-type) | | |
| Water | 60 to 90 preferably | 70 to 90 |
| Surfactant | 0.5 to 10 preferably | 2 to 4 |
| Acaricidal active substance | 0.5 to 10 preferably | 1 to 6 |
| Cellulose | 0.5 to 20 preferably | 1 to 5 |
| Thickener | 0.1 to 2 preferably | 0.2 to 0.3 |
| Propellant | 5 to 20 preferably | 7 to 13 |
| Perfume | 0.2 | |
| Preservative | 0.2 | |
| (IV) Acaricidal upholstery and mattress cleanser (foam-type) | | |
| Water | 10 to 90 preferably | 70 to 90 |
| Surfactant | 0.5 to 10 preferably | 2 to 4 |
| Acaricidal active substance | 0.5 to 10 preferably | 1 to 6 |
| Polymer, 40% | 1 to 80 preferably | 5 to 10 |
| Propellant | 5 to 20 preferably | 7 to 13 |
| Perfume | 0.2 | |
| Preservative | 0.2 | |

The textile surfaces of interior furnishings to be treated with the agent according to the invention are those areas on which the presence of house dust mites was detected. These are in particular carpets, upholstered furniture, beds, including pillows, blankets and bed mattresses. The fibers of the textile substrate can here be of natural and/or synthetic origin.

The agent according to the invention is expediently applied to mattresses or upholstered furniture in such a way that, after the foam-type cleanser has dried, the particles penetrate to a depth of about 1 to 2 cm.

Because of the desired prolonged period of action of the acaricidal active component on the surfaces or objects infested by mites, which period extends over a time of about 2 to 3 weeks, as explained above, it is advantageous to repeat the treatment with the agent according to the invention once or twice within this period. In this way, the particular mite populations are dealt with in an efficaceous manner.

The examples which follow explain the invention without restricting its application.

EXAMPLE 1

| Acaricidal carpet cleaner (liquid) | |
|---|---|
| Water, distilled | 66.48% |
| Antifoam ($C_{12}$-$C_{18}$—fatty acid and 45% sodium hydroxide solution) | 0.7 |
| Triethanolamine | 2.00 |
| Surfactant mixture (sodium lauryl ethersulfate, alkylphenol ethoxylate) | 4.62 |
| Benzyl benzoate | 6.00 |
| Polyacrylate, 40% | 20.00 |
| Preservative | 0.20 |

| Acaricidal carpet cleaner (liquid) | |
|---|---|
| | 100.00% |

EXAMPLE 2

| Acaricidal upholstery and mattress cleanser (foam-type) | |
|---|---|
| Water, distilled | 85.3% |
| Surfactant mixture (sodium lauryl-sulfate, alkenesulfonate, hydroxyalkanesulfonate, soap) | 3.4 |
| Benzyl benzoate | 2.00 |
| Cellulose | 2.00 |
| Organic polymer (xanthan gum) | 0.30 |
| Propane/butane | 7.0 |
| | 100.00% |

EXAMPLE 3

| Acaricidal upholstery and mattress cleanser (foam-type) | |
|---|---|
| Water, distilled | 73.6% |
| Surfactant mixture (as Example 2) | 2.8 |
| Benzyl benzoate | 2.6 |
| Polyacrylate, 40% | 8.0 |
| Propane/butane | 13.0 |
| | 100.0% |

EXAMPLE 4

| Acaricidal textile cleanser (pulverulent) | |
|---|---|
| Cellulose powder | 30.0% |
| Crystal quartz sand | 30.0 |
| Sodium chloride | 2.0 |
| White spirit | 12.0 |
| Water, distilled | 15.8 |
| Preservative | 0.20 |
| $SiO_2$ (diatomaceous earth) | 5.00 |
| Benzyl benzoate | 5.00 |
| | 100.00% |

The above agents according to the invention were investigated with respect to their efficacy against house dust mites. The tests carried out in the laboratory gave the followng result:

1. Cleanser according to Example 1

At an application concentration of 3 to 5 percent by weight of benzoyl benzoate in water, the resulting mortality rate of the house dust mites after 8 days was 77.8% (test 1) or 99.9% (test 2).

2. Agent according to Example 2

The application of this foam in a quantity of 50 to 100 g/m² of textile surface area gave a mortality rate of the house dust mites after 1 day of 100% (test 1) and 100% (test 2).

3. Agent according to Example 3

Application of this foam in a quantity of 50 to 100 g/m² of textile surface area gave a mortality rate of the house dust mites after 1 day of 100%.

4. Agent according to Example 4

When this was applied as a powder in a quantity of 30 to 50 g/m² of textile surface area, the mortality rate of the house dust mites after one day and after 8 days was 99.9% in each case.

With the mortality rates given above, the percentage data always relate to the mite population present.

These tests were carried out in the biological laboratory under practical conditions, and were repeated several times. The indicated efficacy figures were always confirmed.

We claim:

1. A cleansing composition for treating textile surfaces of interior furnishings, said composition containing an acaricidal agent effective against house dust mites and also toxicologically acceptable to humans contacting the treated textile surfaces, said composition comprising:
   at least benzyl benzoate as the acaricidal agent,
   a solid component and
   a cleansing ingredient,
   said solid component causing the cleaning composition after application to the treated surface to leave a pulverulent residue having a mean particle size suitable for ingestion by the house dust mites, said composition being formulated in such proportions as not significantly to increase the tendency of the treated textile surface to pick up dirt.

2. A composition as claimed in claim 1, the pulverulent residue of which has a mean particle size of 2 to 100 µm.

3. A composition as claimed in claim 1, wherein the combination of acaricidal active compound and cleansing ingredient is matched such that the resulting pulverulent residue is ingested as fodder by the mites, without repelling them.

4. A composition as claimed in claim 1, which is free of polyalkylene glycols, ethers and esters thereof, and free of fatty acid esters.

5. The composition of claim 1, which is in the form of a liquid or foam-type cleansing composition with water as the predominant liquid carrier, the solid component being a plastic dissolved or dispersed in the liquid carrier, said plastic after drying giving the mean particle size.

6. The composition according to claim 5, in which the mean particle size is of 2 to 100 µm.

7. The composition to claim 1, which is in the form of a powder, said powder having a liquid content with water as the predominant liquid carrier, said solid component being a plastic having said suitable mean particle size.

8. The composition according to claim 7, in which the mean particle size is of 2 to 100 µm.

9. The composition of claim 1, which is in the form of a liquid or foam-type cleansing composition with water as the predominant liquid carrier, the solid component being an inorganic or organic solid powder having the suitable mean particle size.

10. The composition according to claim 9, in which the mean particle size is 2 to 100 µm.

11. A composition according to claim 1, which is in the form of a powder, said powder having a liquid content with water as the predominant liquid carrier, said solid component being an inorganic or organic solid powder having the suitable mean particle size.

12. The composition according to claim 11, in which the mean particle size is 2 to 100 µm.

13. A method for treating surfaces of textiles in interior furnishings so as to kill house dust mites which come in contact with said surfaces which comprises applying thereto a composition according to claim 1.

14. A method for treating surfaces of textiles in interior furnishings so as to kill house dust mites which come in contact with said surfaces which comprises applying thereto a composition according to claim 5.

15. A method for treating surfaces of textiles in interior furnishings so as to kill house dust mites which come in contact with said surfaces which comprises applying thereto a composition according to claim 7.

16. A method for treating surfaces of textiles in interior furnishings so as to kill house dust mites which come in contact with said interior textiles surfaces which comprises applying thereto a composition according to claim 9.

17. A method for treating surface of textiles in interior furnishings so as to kill house dust mites which come in contact with said interior textile surfaces which comprises applying thereto a composition according to claim 11.

* * * * *